(12) United States Patent
Arlt et al.

(10) Patent No.: US 8,288,558 B2
(45) Date of Patent: Oct. 16, 2012

(54) METATHESIS CATALYSTS

(75) Inventors: Dieter Arlt, Rinteln (DE); Michal Bieniek, Wroclaw (PL); Ralf Karch, Kleinostheim (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 561 days.

(21) Appl. No.: 12/440,993

(22) PCT Filed: Sep. 13, 2007

(86) PCT No.: PCT/EP2007/007972
§ 371 (c)(1),
(2), (4) Date: Oct. 26, 2009

(87) PCT Pub. No.: WO2008/034552
PCT Pub. Date: Mar. 27, 2008

(65) Prior Publication Data
US 2010/0113795 A1 May 6, 2010

(30) Foreign Application Priority Data
Sep. 18, 2006 (DE) .................. 10 2006 043 704

(51) Int. Cl.
*C07F 15/00* (2006.01)
(52) U.S. Cl. ...................................... 548/103
(58) Field of Classification Search .......... 548/103
See application file for complete search history.

(56) References Cited

FOREIGN PATENT DOCUMENTS
WO 2005/016944 A 2/2005
WO WO 2005/016944 * 2/2005

OTHER PUBLICATIONS

Wakamatsu H et al., "A new highly efficient ruthenium metathesis catalyst", vol. 114, No. 13, 2002, pp. 2509 & 2511.
Bujok, R et al., "Ortho-and para-substituted Hoveyda-grubbs carbenes . . . "J. Org. Chem., vol. 69, 2004, pp. 6894-6896.
Bieniek M. et al., "Advanced fine tuning of Grubbs/Hoveyda olefin metathesis . . . "J. Am. Chem, vol. 128, 2006, pp. 13652-13653.
Wakamatsu H et al., "A new highly efficient ruthenium metathesis catalyst" vol. 114, No. 13, 2002, pp. 2509-2511.
Bujok, R. et al., "Ortho-and para-substitued Hoveyda-grubbs carbenes . . . "J. Org. Chem., vol. 69, 2004, pp. 6894-6896.
Bieniek, M. et al., "Advanced fine-tuning of Grubbs/Hoveyda olefin metathesis . . . " J. Am. Chem., vol. 128, 2006, pp. 13652-13653.
International Search Report, PCT/EP2007/007972, Jan. 2008.

* cited by examiner

*Primary Examiner* — Joseph Kosack
(74) *Attorney, Agent, or Firm* — Smith, Gambrell & Russell, LLP

(57) ABSTRACT

The present invention relates to novel compounds of the formula 1, their preparation, intermediates for the preparation and the use of the compounds of the formula 1 as catalysts in various metathesis reactions.
The novel metathesis catalysts, which are obtained from readily available precursors, have a high activity and can be used for any type of metathesis reaction.

8 Claims, 1 Drawing Sheet

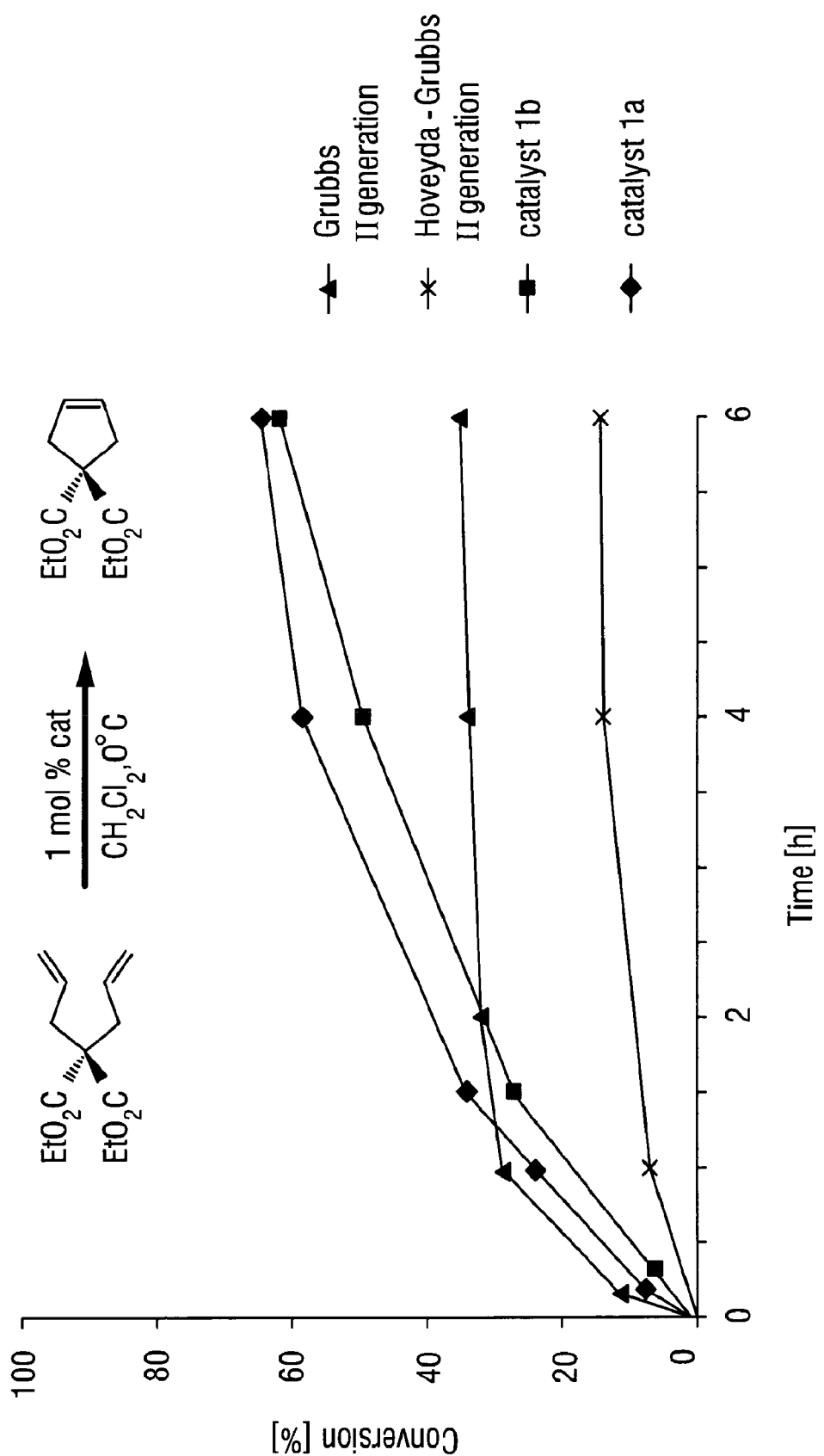

METATHESIS CATALYSTS

The present invention relates to a novel compound of the formula 1, its preparation, intermediates for the preparation and the use of the compounds of the formula 1 as catalysts in various metathesis reactions.

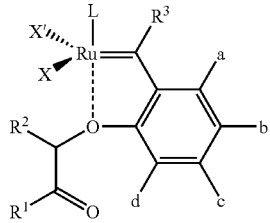

1

BACKGROUND OF THE INVENTION

Ruthenium complexes of the formula A are known from WO 02/14376 A2 and are described as active, air-stable and recoverable metathesis catalysts. Further catalysts of this type which are described by the formulae B, C and I) and have an even higher activity than A have become known (Angew. Chem. 2002, 114 No. 5, 832-834; Angew. Chem. 2002, 114, No. 13, 2509-2511; Angew. Chem. 2002, 114, No. 21, 4210-4212).

The improvement in the activity of B and C compared to A is attributed to steric and electronic effects of the substituents on the benzene ring, and in the case of D to a specific change in the aliphatic radical of the ether group of the ligand.

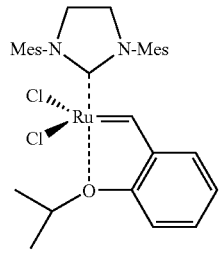

A

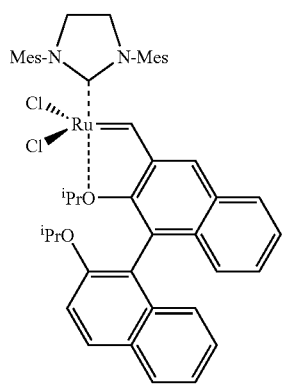

B

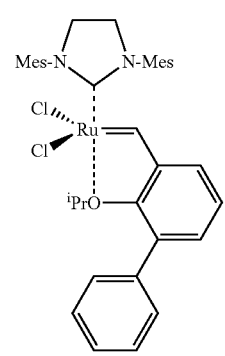

C

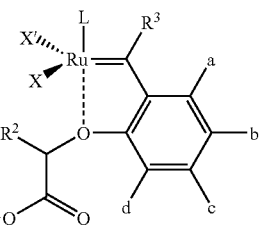

D

It has now surprisingly been found that a further increase in the activity of ruthenium catalysts of the formula A can be achieved, even compared to D, by introducing a keto group into the aliphatic radical of the ether group of the ligand.

DETAILED DESCRIPTION OF THE INVENTION

The present invention provides novel ruthenium complexes of the formula 1 and their use as metathesis catalysts,

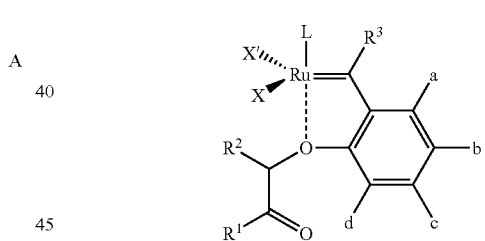

1 where

X and X' are anionic ligands; preferably halogen, particularly preferably Cl or Br;

L is an uncharged ligand;

a, b, c, d are each, independently of one another, H, $-NO_2$, $C_{1-12}$-alkyl, $C_{1-12}$-alkoxy or phenyl, where phenyl may be substituted by a radical selected from the group consisting of $C_{1-6}$-alkyl and $C_{1-6}$-alkoxy;

$R^1$ is $C_{1-12}$-alkyl, $C_{5-6}$-cycloalkyl, $C_{7-18}$-aralkyl, aryl;

$R^2$ is H, $C_{1-12}$-alkyl, $C_{5-6}$-cycloalkyl, $C_{7-18}$-aralkyl, aryl;

$R^3$ is H, $C_{2-12}$-alkenyl, $C_{2-12}$-alkynyl, aryl.

Preference is given here to the compounds of the formula 1 in which

X and X' are each halogen;

L is an uncharged ligand;

a, b, c, d are each, independently of one another, II, $-NO_2$, $C_{1-6}$-alkyl, $C_{1-6}$-alkoxy or phenyl, where phenyl may be substituted by a radical selected from the group consisting of $C_{1-4}$-alkyl and $C_{1-4}$-alkoxy;

$R^1$ is $C_{1-6}$-alkyl, $C_{5-6}$-cycloalkyl, $C_{7-11}$-aralkyl, aryl;
$R^2$ is H, $C_{1-6}$-alkyl, $C_{5-6}$-cycloalkyl, $C_{7-11}$-aralkyl, aryl;
$R^3$ is H, $C_{1-6}$-alkyl, $C_{2-6}$-alkenyl, $C_{2-6}$-alkynyl, aryl;
among which particular preference is given to the compounds of the formula 1 in which
X and X' are each Cl or Br;
L is an uncharged ligand;
a, b, c, d are each, independently of one another, H, —$NO_2$, methyl, ethyl, isopropyl, methoxy or phenyl, where phenyl may be substituted by a radical selected from the group consisting of methyl and methoxy;
$R^1$ is methyl, ethyl, n-propyl, isopropyl, n-butyl, sec-butyl, tert-butyl, n-heptyl, cyclopentyl, cyclohexyl, 2-methylcyclohexyl, 2,4-dimethylcyclohexyl, benzyl, 1-phenylethyl, 2-phenylethyl, phenyl, o-, m-, p-tolyl and 3,5-dimethylphenyl;
$R^2$ is H, methyl, ethyl, n-propyl, isopropyl, n-butyl, sec-butyl, tert-butyl, n-heptyl, cyclopentyl, cyclohexyl, 2-methylcyclohexyl, 2,4-dimethylcyclohexyl, benzyl, 1-phenylethyl, 2-phenylethyl, phenyl, o-, m-, p-tolyl and 3,5-dimethylphenyl,
$R^3$ is H, methyl, ethyl, phenyl.

Among the abovementioned compounds of the general formula 1, particular preference is given to those in which $R^1$, $R^2$, $R^3$, X, X' and L can have the stated meanings and
a, b, c are each H and
d is phenyl which may be substituted by a radical selected from the group consisting of $C_{1-6}$-alkyl and $C_{1-6}$-alkoxy;
or
a, c, d are each H and
b is —$NO_2$.

Furthermore, particular preference is given among the abovementioned compounds of the general formula 1 to those in which $R^1$, $R^2$, $R^3$, X, X', a, b, c and d can have the stated meanings and
L is $P(R^4)_3$ or a ligand of the formula $L^1$, $L^2$, $L^3$ or $L^4$,

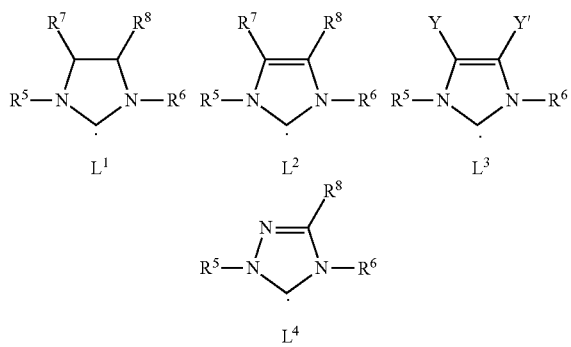

where
$R^4$ is $C_{1-6}$-alkyl, cycloalkyl or aryl,
$R^5$ and $R^6$ are each, independently of one another, H, $C_{1-6}$-alkyl or aryl,
$R^7$ and $R^8$ are each, independently of one another, H, $C_{1-6}$-alkyl, $C_{2-6}$-alkenyl or aryl; or
$R^7$ and $R^8$ together form a 3- or 4-membered alkylene bridge; and
Y and Y' are each halogen; preferably Cl or Br.

Most preferred are compounds of the general formula 1 in which
X and X' are each Cl;
L is $L^1$;
a, b, c, d are each H;
$R^1$ is methyl;
$R^2$ is H;
$R^3$ is H;
$R^5$ and $R^6$ are each mesityl;
$R^7$ and $R^8$ are each H.

Furthermore, the invention also provides, in further embodiments, compounds of the general formula 1 in which X, X', L and also $R^1$, $R^2$ and $R^3$ have the meanings given in claim 1 and
a, b, c, d can each be, independently of one another, H, —$NO_2$, $C_{1-12}$-alkyl, $C_{1-12}$-alkoxy or phenyl, where phenyl may be substituted by a radical selected from the group consisting of $C_{1-6}$-alkyl and $C_{1-6}$-alkoxy;
halogen; cyano; aryl or heteroaryl;
monohalogenated or polyhalogenated aryl radicals or heteroaryl radicals (e.g. —$C_6F_5$, —$C_6H_4F$ or —$C_6H_3F_2$); monohalogenated or polyhalogenated $C_{1-6}$-alkyl radicals (e.g. —$CF_3$, —$C_2F_5$);
monohalogenated or polyhalogenated $C_{1-6}$-alkyl-substituted aryl radicals (e.g. —$C_6H_4$—$CF_3$, —$C_6H_4$—$C_4F_7$); $C_{1-6}$-alkylcarbonyl radicals;
monohalogenated or polyhalogenated $C_{1-6}$-alkylcarbonyl radicals;
$C_{1-16}$-alkoxycarbonyl radicals; monohalogenated or polyhalogenated $C_{1-6}$-alkoxycarbonyl radicals; arylcarbonyl radicals;
monohalogenated or polyhalogenated arylcarbonyl radicals;
aryloxycarbonyl radicals; monohalogenated or polyhalogenated aryloxycarbonyl radicals;
—(C=O)—$N(R^a)_2$ radicals (where $R^a$ is a $C_{1-6}$-alkyl or aryl radical, in particular a halogenated $C_{1-6}$-alkyl or aryl radical);
—NH—(C=O)—$R^a$ radicals (where $R^a$ is a $C_{1-6}$-alkyl or aryl radical; in particular a halogenated $C_{1-6}$-alkyl or aryl radical);
$C_{1-6}$-alkylsulfonyl radicals (e.g. $CH_3SO_2$—);
$C_{1-6}$-alkylsulfinyl radicals (e.g. $CH_3$—S(O)—);
—P(=O)$(R^a)_2$ radicals (where $R^a$ is a $C_{1-4}$-alkyl or aryl radical, in particular a halogenated $C_{1-6}$-alkyl or aryl radical);
—$SO_2$—NH—$SO_2$—$R^a$ radicals (where $R^a$ is a $C_{1-6}$-alkyl or aryl radical, in particular a halogenated $C_{1-6}$-alkyl or aryl radical);
—N[($SO_2$)$R^a$]$_2$ radicals (where $R^a$ is a $C_{1-6}$-alkyl or aryl radical, in particular a halogenated $C_{1-6}$-alkyl or aryl radical).

The novel compounds of the general formula 1 are obtained by reacting preligands of the formula 2 with ruthenium complexes of the formula 3:

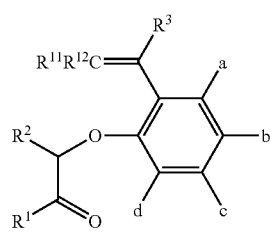

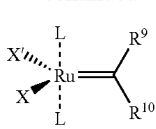

where, in particular embodiments of the reaction, $R^3$, a, b, c and d have the meanings given in claim 1 and $R^1$ is $C_{1-12}$-alkyl, $C_{5-6}$-cycloalkyl, $C_{7-18}$-aralkyl, aryl; preferably $C_{1-6}$-alkyl, $C_{5-6}$-cycloalkyl, $C_{7-11}$-aralkyl, aryl;

$R^2$ is H, $C_{1-12}$-alkyl, $C_{5-6}$-cycloalkyl, $C_{7-18}$-aralkyl, aryl; preferably $C_{1-6}$-alkyl, $C_{5-6}$-cycloalkyl, $C_{7-11}$-aralkyl, aryl;

$R^{11}$ and $R^{12}$ are each, independently of one another, H, $C_{1-6}$-alkyl, if appropriate substituted by one or more halogens, or aryl, if appropriate substituted by one or more halogens or $C_{1-6}$-alkyl; preferably H, $C_{1-6}$-alkyl or aryl;

L is an uncharged ligand; preferably $L^1$, $L^2$, $L^3$ or $L^4$;

$R^9$ and $R^{10}$ are each, independently of one another, H, $C_{1-6}$-alkyl, if appropriate substituted by one or more halogens, or aryl, if appropriate substituted by one or more halogens or $C_{1-6}$-alkyl; preferably H, $C_{1-6}$-alkyl or aryl.

In a preferred embodiment of the reaction, ruthenium complexes of the formula 3 in which the radicals $R^9$ and $R^{10}$ form a ring system (for example an indenylidene system) are used.

In a further preferred embodiment of the reaction, compounds of the general formula 2 in which the substituents a, b, c and d have the meanings given in claim 9 are used.

The invention therefore further provides a compound of the formula 2

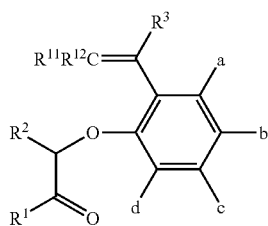

where, in a particular embodiment, $R^3$, a, b, c and d have the meanings given in claim 1; and $R^1$ is $C_{1-12}$-alkyl, $C_{5-6}$-cycloalkyl, $C_{7-18}$-aralkyl, aryl;

$R^2$ is H, $C_{1-12}$-alkyl, $C_{5-6}$-cycloalkyl, $C_{7-18}$-aralkyl, aryl;

$R^{11}$ and $R^{12}$ are each, independently of one another, H, $C_{1-6}$-alkyl, if appropriate substituted by one or more halogens, or aryl, if appropriate substituted by one or more halogens or $C_{1-6}$-alkyl.

Preference is given here to the compounds of the formula 2, in which.

$R^1$ is $C_{1-6}$-alkyl, $C_{5-6}$-cycloalkyl, $C_{7-11}$-aralkyl, aryl;

$R^2$ is H, $C_{1-12}$-alkyl, $C_{5-6}$-cycloalkyl, $C_{7-11}$-aralkyl, aryl;

$R^{11}$ and $R^{12}$ are each, independently of one another, H, $C_{1-4}$-alkyl, if appropriate substituted by one or more halogens, or aryl, if appropriate substituted by one or more halogens or methyl.

Particular preference is given to the compounds of the formula 2 in which $R^1$ is methyl, cyclohexyl, benzyl, phenyl;

$R^2$ is H, methyl, cyclohexyl, benzyl, phenyl;

$R^{11}$ is H;

$R^{12}$ is H or methyl.

Furthermore, the invention also encompasses, in further preferred embodiments, compounds of the formula 2 in which $R^3$ has the meanings given in claim 1 and $R^1$, $R^2$, $R^{11}$ and $R^{12}$ have the meanings given in claim 8 and a, b, c, d can each be, independently of one another, H, —$NO_2$, $C_{1-12}$-alkyl, $C_{1-12}$-alkoxy or phenyl, where phenyl may be substituted by a radical selected from the group consisting of $C_{1-6}$-alkyl and $C_{1-6}$-alkoxy;

halogen; cyano; aryl or heteroaryl;

monohalogenated or polyhalogenated aryl radicals or heteroaryl radicals (e.g. —$C_6F_5$, —$C_6H_4F$ or —$C_6H_3F_2$); monohalogenated or polyhalogenated $C_{1-6}$-alkyl radicals (e.g. —$CF_3$, —$C_2F_5$); monohalogenated or polyhalogenated $C_{1-6}$-alkyl-substituted aryl radicals (e.g. —$C_6H_4$—$CF_3$, —$C_6H_4$—$C_4F_7$); $C_{1-6}$-alkylcarbonyl radicals;

monohalogenated or polyhalogenated $C_{1-6}$-alkylcarbonyl radicals;

$C_{1-6}$-alkoxycarbonyl radicals; monohalogenated or polyhalogenated $C_{1-6}$-alkoxycarbonyl radicals; arylcarbonyl radicals;

monohalogenated or polyhalogenated arylcarbonyl radicals;

aryloxycarbonyl radicals; monohalogenated or polyhalogenated aryloxycarbonyl radicals;

—(C=O)—N($R^a$)$_2$ radicals (where $R^a$ is a $C_{1-6}$-alkyl or aryl radical, in particular a halogenated $C_{1-6}$alkyl or aryl radical);

—NH—(C=O)—$R^a$ radicals (where $R^a$ is a $C_{1-6}$-alkyl or aryl radical; in particular a halogenated $C_{1-6}$-alkyl or aryl radical);

$C_{1-6}$-alkylsulfonyl radicals (e.g. $CH_3SO_2$—);

$C_{1-6}$-alkylsulfinyl radicals (e.g. $CH_3$—S(O)—);

—P(=O)($R^a$)$_2$ radicals (where $R^a$ is a $C_{1-6}$-alkyl or aryl radical, in particular a halogenated $C_{1-6}$-alkyl or aryl radical);

—$SO_2$—NH—$SO_2$—$R^a$ radicals (where $R^a$ is a $C_{1-6}$-alkyl or aryl radical, in particular a halogenated $C_{1-6}$-alkyl or aryl radical);

—N[($SO_2$)$R^a$]$_2$ radicals (where $R^a$ is a $C_{1-6}$-alkyl or aryl radical, in particular a halogenated $C_{1-6}$-alkyl or aryl radical).

The ligands and complexes disclosed can occur as pure enantiomers or enantiomer pairs. The invention therefore encompasses not only any racemates but likewise the pure enantiomers which can transfer their asymmetry to a substrate during catalysis as a result of the asymmetric center.

An additional aspect of the invention is a process for carrying out metathesis reactions in which two compounds which each contain an olefinic double bond or one of the compounds contains at least two olefinic double bonds are reacted and in which one of the abovementioned compounds of the formula 1 is used as catalyst, and also a process for carrying out a ring-closing metathesis (RCM) or a cross methathesis (CM) in which a compound containing two olefinic double bonds as substrate and one of the compounds of the formula 1 as catalyst participate.

TERMS AND DEFINITIONS USED

For the purposes of the invention, the term "anionic ligand" (X or X') refers to negatively charged molecules or atoms having electron donor properties. Examples which may be mentioned are halogens such as fluorine, chlorine, bromine or iodine.

For the purposes of the invention, the term "uncharged ligand" (L) refers to uncharged or apparently charge-neutral molecules or atoms having electron donor properties. Examples which may be mentioned are tertiary phosphines containing aliphatic, cycloaliphatic and aromatic hydrocarbon radicals, e.g. trioctylphosphine, tridodecylphosphine, tricyclohexylphosphine, tris(2-methylcyclohexyl)phosphine and tris(o-tolyl)phosphine. Particularly preferred uncharged ligands are NHC ligands such as the compounds described by the formulae $L^1$, $L^2$, $L^3$ and $L^4$:

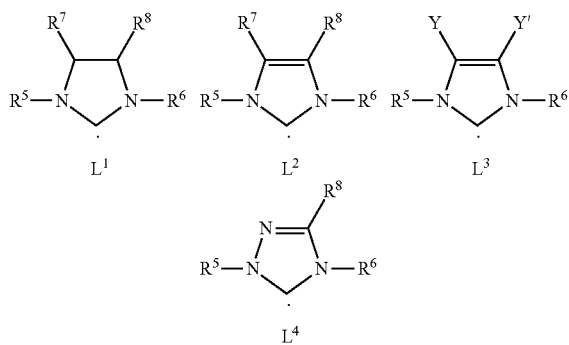

where $R^5$ and $R^6$ are each, independently of one another, H, $C_{1-6}$-alkyl or aryl, $R^7$ and $R^8$ are each, independently of one another, H, $C_{1-6}$-alkyl, $C_{1-6}$-alkenyl or aryl or together form a 3- or 4-membered alkylene bridge and Y and Y' are each halogen.

The term "$C_{1-12}$-alkyl" refers (also when this is a constituent of other radicals) to branched and unbranched alkyl groups having from 1 to 12 carbon atoms; correspondingly, the term "$C_{1-6}$-alkyl" refers to branched and unbranched alkyl groups having from 1 to 6 carbon atoms and the term "$C_{1-4}$-alkyl" refers to branched and unbranched alkyl groups having from 1 to 4 carbon atoms. Preference is given to alkyl groups having from 1 to 6 carbon atoms, particularly preferably from 1 to 4 carbon atoms. Examples which may be mentioned are: methyl, ethyl, n-propyl, isopropyl, n-butyl, isobutyl, sec-butyl, tert-butyl, n-pentyl, isopentyl, neopentyl and hexyl. The abbreviations Me, Et, n-Pr, i-Pr, n-Bu, i-Bu, t-Bu, etc., may also be used for the abovementioned groups. Unless indicated otherwise, in the case of propyl, butyl, pentyl and hexyl, the definitions encompass all conceivable isomeric forms of the respective radicals. Thus, for example, propyl encompasses n-propyl and isopropyl, butyl encompasses isobutyl, sec-butyl and tert-butyl, etc.

The term "$C_{2-12}$-alkenyl" refers (also when it is a constituent of other radicals) to branched and unbranched alkenyl groups having from 2 to 12 carbon atoms, as long as they have at least one double bond. Correspondingly, the term "$C_{2-6}$-alkenyl" refers to alkenyl groups having from 2 to 6 carbon atoms and the term "$C_{2-4}$-alkenyl" refers to branched and unbranched alkenyl groups having from 2 to 4 carbon atoms. Preference is given to alkenyl groups having from 2 to 6 carbon atoms, particularly preferably from 2 to 4 carbon atoms. Examples which may be mentioned are: ethenyl and vinyl, propenyl, butenyl, pentenyl and hexenyl. Unless indicated otherwise, in the case of propenyl, butenyl, pentenyl and hexenyl, the definitions encompass all conceivable isomeric forms of the respective radicals. Thus, for example, propenyl encompasses 1-propenyl and 2-propenyl, butenyl encompasses 1-, 2- and 3-butenyl, 1-methyl-1-propenyl, 1-methyl-2-propenyl, etc.

The term "$C_{2-12}$-alkynyl" refers (also when it is a constituent of other radicals) to branched and unbranched alkynyl groups having from 2 to 12 carbon atoms, as long as they have at least one triple bond. Correspondingly, the term "$C_{2-6}$-alkynyl" refers to alkynyl groups having from 2 to 6 carbon atoms and the term "$C_{2-4}$-alkynyl" refers to branched and unbranched alkynyl groups having from 2 to 4 carbon atoms. Preference is given to alkynyl groups having from 2 to 6 carbon atoms, particularly preferably from 2 to 4 carbon atoms. Examples which may be mentioned are: ethynyl, propynyl, butynyl, pentynyl and hexynyl. Unless indicated otherwise, in the case of propynyl, butynyl, pentynyl or hexynyl, the definitions encompass all conceivable isomeric forms of the respective radicals. Thus, for example, propynyl encompasses 1-propynyl and 2-propynyl, butynyl encompasses 1-, 2- and 3-butynyl, 1-methyl-1-propynyl, 1-methyl-2-propynyl, etc.

The term "$C_{1-12}$-alkoxy" refers (also when it is a constituent of other radicals) to branched and unbranched alkoxy groups having from 1 to 12 carbon atoms; correspondingly, the term "$C_{1-6}$-alkoxy" refers to branched and unbranched alkoxy groups having from 1 to 6 carbon atoms and the term "$C_{1-4}$-alkoxy" refers to branched and unbranched alkoxy groups having from 1 to 4 carbon atoms. Preference is given to alkoxy groups having from 1 to 6 carbon atoms, particularly preferably from 1 to 4 carbon atoms. Examples which may be mentioned are: methoxy, ethoxy, propoxy, butoxy and pentoxy. The abbreviations MeO, EtO, PrO, etc., may also be used for the abovementioned groups. Unless indicated otherwise, in the case of propoxy, butoxy and pentoxy, the definitions encompass all conceivable isomeric forms of the respective radicals. Thus, for example, propoxy encompasses n-propoxy and isopropoxy, butoxy encompasses isobutoxy, sec-butoxy and tert-butoxy, etc.

The term "$C_{5-6}$-cycloalkyl" refers (even when it is a constituent of other radicals) to cyclic alkyl groups having 5 or 6 carbon atoms. Examples which may be mentioned are: cyclopentyl and cyclohexyl. Unless indicated otherwise, the cyclic alkyl groups can be substituted by one or more radicals selected from the group consisting of methyl, ethyl, isopropyl, tert-butyl, hydroxy, fluorine, chlorine, bromine and iodine.

The term "aryl" refers (also when it is a constituent of other radicals) to aromatic ring systems having 6 or 10 carbon atoms. Examples which may be mentioned are: phenyl and naphthyl; the preferred aryl radical is phenyl. Unless indicated otherwise, the aromatics can be substituted by one or more radicals selected from the group consisting of methyl, ethyl, isopropyl, tert-butyl, hydroxy, fluorine, bromine and iodine.

The term "$C_{7-18}$-aralkyl" refers (also when it is a constituent of other radicals) to branched and unbranched alkyl groups which have from 1 to 8 carbon atoms and are substituted by an aromatic ring system having 6 or 10 carbon atoms; correspondingly, the term "$C_{7-11}$-aralkyl" refers to branched and unbranched alkyl groups which have from 1 to 4 carbon atoms and are substituted by an aromatic ring system having 6 carbon atoms. Examples which may be mentioned are: benzyl, 1- and 2-phenylethyl.

Unless indicated otherwise, the aromatics can be substituted by one or more radicals selected from the group consisting of methyl, ethyl, isopropyl, tert-butyl, hydroxy, fluorine, bromine and iodine.

Preparation of the Compounds

The reaction of the ruthenium complexes of the formula 3 with the preligands of the formula 2 is carried out in inert solvents, e.g. $CH_2Cl_2$, at from about 0° to 80° C. It is advantageous to add CuCl to the reaction-mixture. The reactants are generally used in stoichiometric amounts, but the more valuable component in each case can be used in a substoichiometric amount to increase the yield. It can also be advantageous to generate the complex of the formula 3 in situ from other ruthenium compounds and ligand precursors, e.g. dihydroimidazolinium salts, and proceed via the resulting complexes of the formula 3 in order to arrive at the novel metathesis catalysts of the formula 1 having the ligand combination desired in each case.

The metathesis catalysts of the formula 1 prepared by the ligand exchange reaction can be separated off from other reaction products which are insoluble in the reaction mixture by filtration of their solution and, after evaporation of the solution, obtained in pure form by chromatography or crystallization. However, it is also possible to use the crude products or the catalysts generated in situ directly for carrying out metathesis reactions.

The preligands of the formula 2 can be prepared in a manner known per se from o-alkenylphenols by alkylation using α-haloketones.

Particular preference is given to a novel combined process which starts out from unsubstituted or appropriately substituted phenyl allyl ethers which are subjected to Claisen rearrangement and catalytic double bond isomerization to give unsubstituted or appropriately substituted 2-alkenylphenols which are subsequently converted into compounds of the formula 2 by alkylation using α-haloketones.

The alkylation of phenols to form alkyl phenyl ethers is well known to those skilled in the art; it is usually carried out in solvents in the presence of basic substances by reaction with nucleophilic reagents. The reaction with α-haloketones proceeds particularly smoothly and in good yields. Possible solvents are, for example, alcohols such as ethanol or aprotic polar solvents such as dimethylformamide. The alkylation can also be carried out under phase transfer conditions. Basic substances which may be mentioned are alkali metal carbonates, and it is likewise possible to use the alkali metal salts of the intermediates containing a free aromatically bound OH group for this reaction. The following examples illustrate the invention.

EXAMPLE 1

Preparation of the Metathesis Catalyst of the Formula 1a 1.1 Preparation of the Novel Preligand of the Formula 2a A mixture of 7.112 g (50.0 mmol) of 2-propenylphenol (E/Z mixture), 7.041 g of potassium carbonate (50.0 mmol) and 20 ml of acetone was stirred at the boiling point under reflux for 20 minutes. A mixture of 6.94 g (75.0 mmol) of chloroacetone, 0.171 g (1.0 mmol) of potassium iodide and 6.5 ml of acetone which had been activated beforehand by stirring overnight at room temperature was then added to the reaction mixture and the reaction mixture was stirred overnight at the boiling point under reflux. The reaction mixture was cooled to room temperature, added to 50 ml of water and extracted three times with 40 ml each time of diethyl ether. The organic phase was washed with 5% strength sodium hydroxide solution, separated off, dried over $Na_2SO_4$ and evaporated. Distillation of the crude product under reduced pressure gave 6.788 g (yield: 67% of theory) of 2-propenylphenyloxymethyl methyl ketone of the formula 2a:

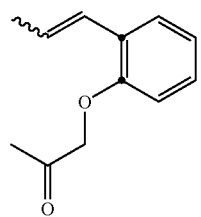

$^1$H NMR (400 MHz, $CDCl_3$) (Z isomer): δ 1.84 (dd, 3H, J=7.0, 1.8 Hz), 2.30 (s, 3H), 4.52 (s, 2H), 5.88 (dq, 1H, J=11.6, 7.2 Hz), 6.61 (dq, 1H, J=11.6, 1.8 Hz), 6.73 (dd, 1H, J=8.2, 0.9 Hz), 6.93-7.02 (m, 1H), 7.18-7.24 (m, 1H), 7.31 (dd, 1H, J=7.5, 1.7 Hz); $^1$H NMR (400 MHz, $CDCl_3$) (E isomer): δ 1.92 (dd, 3H, J=6.7, 1.8 Hz), 2.31 (s, 3H), 4.54 (s, 2H), 6.27 (dq, 1H, J=15.9, 6.7 Hz), 6.68 (dd, 1H, J=1.1, 8.2 Hz), 6.61 (dq, 1H, J=15.9, 1.7 Hz), 6.92-7.02 (m, 0.1H), 7.12-7.18 (m, 1H), 7.42 (dd, 1H, J=7.6, 1.7 Hz).

1.2 Preparation of the Metathesis Catalyst of the Formula 1a 62 mg (0.32 mmol) of the compound 2a, 34 mg (0.34 mmol) of CuCl and 12 ml of dichloromethane were placed in a Schlenk tube. 230 mg (0.27 mmol) of Grubbs catalyst, 2nd generation, were then added. The reaction mixture was stirred at the reflux temperature under argon for 20 minutes. The crude product obtained after filtration and evaporation of the solvent was purified by chromatography. (Silica gel Merck grade 9385, eluent: AcOEt/cyclohexane 1:1). This gave 142 mg (82% of theory) of the pure catalyst of the formula 1a.

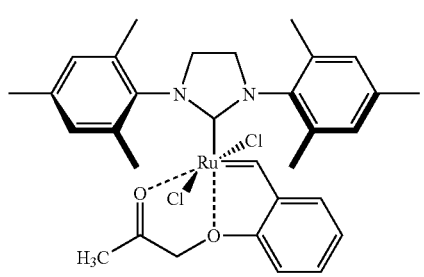

LRMS (EI): m/e=641 (1, M$^+$), 404 (1), 324 (6), 305 (22), 280 (8), 252 (2), 198 (34), 145 (7), 131 (11), 118 (100), 115 (16), 105 (9), 89 (38), 81 (10), 73 (18), 63(19), 55(22), 43 (39), 36 (30).

EXAMPLE 2

Preparation of the Metathesis Catalyst of the Formula 1b

Using a procedure analogous to that described in example 1, the preligand 2-propenyl-phenyloxymethyl ethyl ketone was obtained by reaction of 2-propenylphenol (E/Z mixture) with chloromethyl ethyl ketone. Reaction of this preligand with Grubbs catalyst, 2nd generation, led to the catalyst of the formula 1b in a yield of 63% of theory (pure product).

LRMS (EI): m/e=656 (2), 654 (2, M+), 406 (3), 404 (3), 308 (5), 307 (23), 305 (32), 304 (62), 303 (57), 289 (12), 190 (15), 178 (16), 159 (10), 158 (18), 157 (14), 148 (28), 147 (16), 145 (10), 144 (8), 133 (21), 131 (20), 121 (16), 120 (11), 119 (25), 118 (100), 107 (19), 105 (18), 103 (11), 91 (57), 90 (38), 89 (40), 77 (18), 65 (11), 63 (20), 57 (91), 51 (13), 43 (31), 41(14), 39 (19), 36 (31); HRMS (EI): calculated for $C_{32}H_{38}O_2N_2$ $^{35}Cl_2$ $^{102}Ru$ (M+): 654.13538; found 654.13790.

COMPARATIVE EXAMPLES

A) Cross Metathesis (CM) of 4-methoxystyrene with (E)-1,2-dichloroethene 0.005 mmol of the catalyst of the formula 1a and (as known catalysts for comparison) of the catalyst of the formula D (see page 2 of the present patent application) and also Grubbs catalyst, 2nd generation, likewise in an amount of 0.005 mmol in each case were in each case added as solids to solutions of (4-methoxystyrene) (0.5 mmol) and (E)-1,2-dichloroethene (1.0 mmol) in 25 ml of dichloromethane. The reaction mixture was in each case heated to 40° C. for 24 hours.

The following yields of cross metathesis product (4-methoxy-ω-chlorostyrene) were determined by GC (internal standard: nonane):

yield using Grubbs catalyst, 2nd generation: 25% of theory yield using the catalyst of the formula D: 35% of theory yield using the catalyst 1a according to the invention: 57% of theory.

B) Comparative Ring-Closing Methathesis (RCM) of Diethyl Bisallylmalonate

A solution of 0.004 mmol of the known metathesis catalysts (Grubbs catalyst, 2nd generation, and Hoveyda-Grubbs catalyst, 2nd generation) and also the catalysts 1a and 1b according to the invention, in each case dissolved in 1 ml of dichloromethane, was in each case added to solutions of 0.4 mmol of diethyl bisallylmalonate (substrate) in ml of dichloromethane. Gas-chromatographic analysis of the RCM (at 0° C.) showed the significantly higher activity of the catalysts 1a and 1b according to the invention (see FIG. 1).

The catalysts according to the invention not only have a superior activity compared to known catalysts of this type but are also air- and storage-stable, which represents a further advantage for industrial usability.

The invention claimed is:

1. A compound of the general formula 1, wherein
X and X' are anionic ligands;
L is a ligand of the formula $L^1$, $L^2$, $L^3$ or $L^4$ or L is a ligand of the formula $P(R^4)_3$, where $R^4$ is $C_{1-6}$-alkyl, cycloalkyl or aryl;
a, b, c, d are each, independently of one another, H, —$NO_2$, $C_{1-12}$-alkyl, $C_{1-12}$-alkoxy or phenyl,
where phenyl may be substituted by a radical selected from the group consisting of $C_{1-6}$-alkyl and $C_{1-6}$-alkoxy;
$R^1$ is $C_{1-12}$-alkyl, $C_{5-6}$-cycloalkyl, $C_{7-18}$-aralkyl, or aryl;
$R^2$ is H, $C_{1-12}$-alkyl, $C_{5-6}$-cycloalkyl, $C_{7-18}$-aralkyl, or aryl;
$R^3$ is H, $C_{2-12}$-alkenyl, $C_{2-12}$-alkynyl, or aryl;
$R^5$ and $R^6$ are each, independently of one another, H, $C_{1-6}$-alkyl or aryl;
$R^7$ and $R^8$ are each, independently of one another, H, $C_{2-6}$-alkenyl or aryl; or
$R^7$ and $R^8$ together form a 3- or 4-membered alkylene bridge; and
Y and Y' are each halogen.

2. The compound of the general formula 1 as claimed in claim 1, wherein a, b, c are each H; and
d is phenyl substituted by a radical selected from the group consisting of $C_{1-6}$-alkyl and $C_{1-6}$-alkoxy.

3. The compound of the general formula 1 as claimed in claim 1, wherein a, b, c and d are each H.

4. The compound of the general formula 1 as claimed in claim 1, wherein X and X' are each Cl;
L is $L^1$;
a, b, c, d are each H;
$R^1$ is methyl;
$R^2$ is H;
$R^3$ is H;

$R^5$ and $R^6$ are each mesityl; and
$R^7$ and $R^8$ are each H.

5. A compound of the general formula 2,

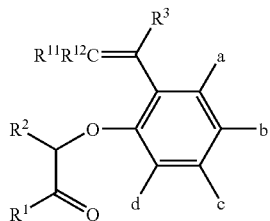

where
a, b, c, d are each, independently of one another, H, —NO$_2$ $C_{1-12}$-alkyl, $C_{1-12}$-alkoxy or phenyl,
where phenyl may be substituted by a radical selected from the group consisting of $C_{1-6}$-alkyl and $C_{1-6}$-alkoxy;
$R^1$ is $C_{1-12}$-alkyl, $C_{5-6}$-cycloalkyl, $C_{7-18}$-aralkyl, or aryl;
$R^2$ is H, $C_{1-12}$-alkyl, $C_{5-6}$-cycloalkyl, $C_{7-18}$-aralkyl, or aryl;
$R^3$ is H, $C_{2-12}$-alkenyl, $C_{2-12}$-alkynyl, or aryl; and
$R^{11}$ and $R^{12}$ are each, independently of one another, H, or $C_{1-6}$-alkyl.

6. A process for preparing the compounds of the general formula 1

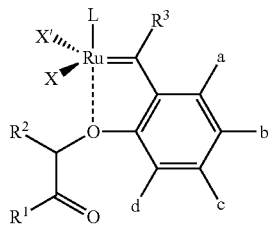

which comprises reacting compounds of the formula 2 with ruthenium complexes of the formula 3:

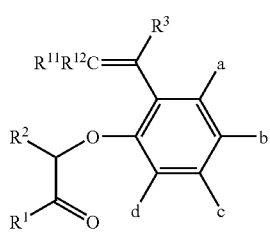

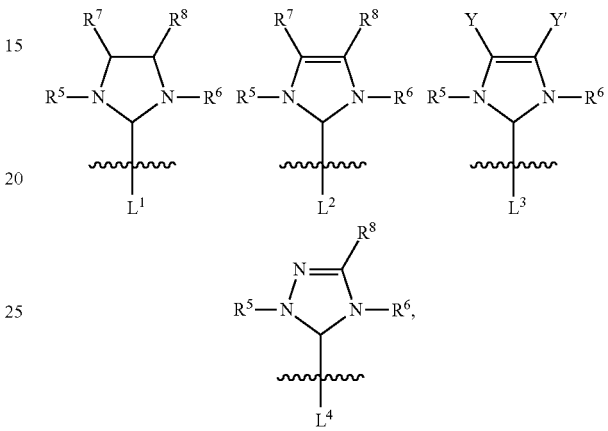

wherein
X and X' are anionic ligands;
L is an uncharged ligand; selected from the group consisting of $L^1$, $L^2$, $L^3$, or $L^4$ or L is a ligand of the formula $P(R^4)_3$;
a, b, c, d are each, independently of one another, H, —NO$_2$, $C_{1-12}$-alkyl, $C_{1-12}$-alkoxy or phenyl,
where phenyl may be substituted by a radical selected from the group consisting of $C_{1-6}$-alkyl and $C_{1-6}$-alkoxy;
$R^1$ is $C_{1-12}$-alkyl, $C_{5-6}$-cycloalkyl, $C_{7-18}$-aralkyl, or aryl;
$R^2$ is H, $C_{1-12}$-alkyl, $C_{5-6}$-cycloalkyl, $C_{7-18}$-aralkyl, or aryl;
$R^3$ is H, $C_{2-12}$-alkenyl, $C_{2-12}$-alkynyl, or aryl;
$R^4$ is $C_{1-6}$-alkyl, cycloalkyl or aryl;
$R^5$ and $R^6$ are each, independently of one another, H, $C_{1-6}$-alkyl or aryl;
$R^7$ and $R^8$ are each, independently of one another, H, $C_{2-6}$-alkenyl or aryl; or $R^7$ and $R^8$ together form a 3- or 4-membered alkylene bridge;
$R^9$ and $R^{10}$ are each, independently of one another, H, $C_{1-6}$-alkyl, or aryl; or $R^9$ and $R^{10}$ form a ring system;
$R^{11}$ and $R^{12}$ are each, independently of one another, H, or $C_{1-6}$-alkyl; and
Y and Y' are each halogen.

7. A process for carrying out a metathesis reaction, which comprises catalyzing the metathesis reaction with a compound according to claim 1.

8. A process for carrying out a reaction which is a ring-closing metathesis (RCM) reaction or a cross metathesis (CM) reaction which comprises catalyzing the reaction with a compound according to claim 1.

* * * * *